United States Patent
McDaniel et al.

(10) Patent No.: US 6,728,331 B1
(45) Date of Patent: Apr. 27, 2004

(54) METHOD AND SYSTEM FOR TRAUMA APPLICATION OF CT IMAGING

(75) Inventors: Holly Ann McDaniel, Waukesha, WI (US); Priya Gopinath, North Arlington, NJ (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/065,457

(22) Filed: Oct. 21, 2002

(51) Int. Cl.⁷ .............................................. G01N 23/00
(52) U.S. Cl. ............................ 378/4; 378/19; 378/901
(58) Field of Search ............................. 379/19, 4, 901, 379/15, 20

(56) References Cited

U.S. PATENT DOCUMENTS 6,366,638 B1 * 4/2002 Hsieh et al. .................. 378/19
6,393,090 B1 * 5/2002 Hsieh et al. ................... 378/4

FOREIGN PATENT DOCUMENTS

EP         1220153 A2    7/2002

* cited by examiner

Primary Examiner—David V. Bruce
Assistant Examiner—Hoon Song
(74) Attorney, Agent, or Firm—Cantor Colburn LLP

(57) ABSTRACT

A method and system for generating a plurality of clinically useful images in a short time frame using a single imaging system. The system and method include using a single computer tomography (CT) system for generating a scout image configured to prescribe a tomographic axial/helical or target image and processing the scout projection data of the scout image to generate an enhanced scout image. The enhanced scout image and the target image are displayed, wherein the enhanced scout image and said target image are clinically useful images for diagnostic purposes provided by the single imaging system. More specifically, the single CT generates the enhanced scout image resembling an x-ray radiograph and the target image as a CT scan image.

30 Claims, 4 Drawing Sheets

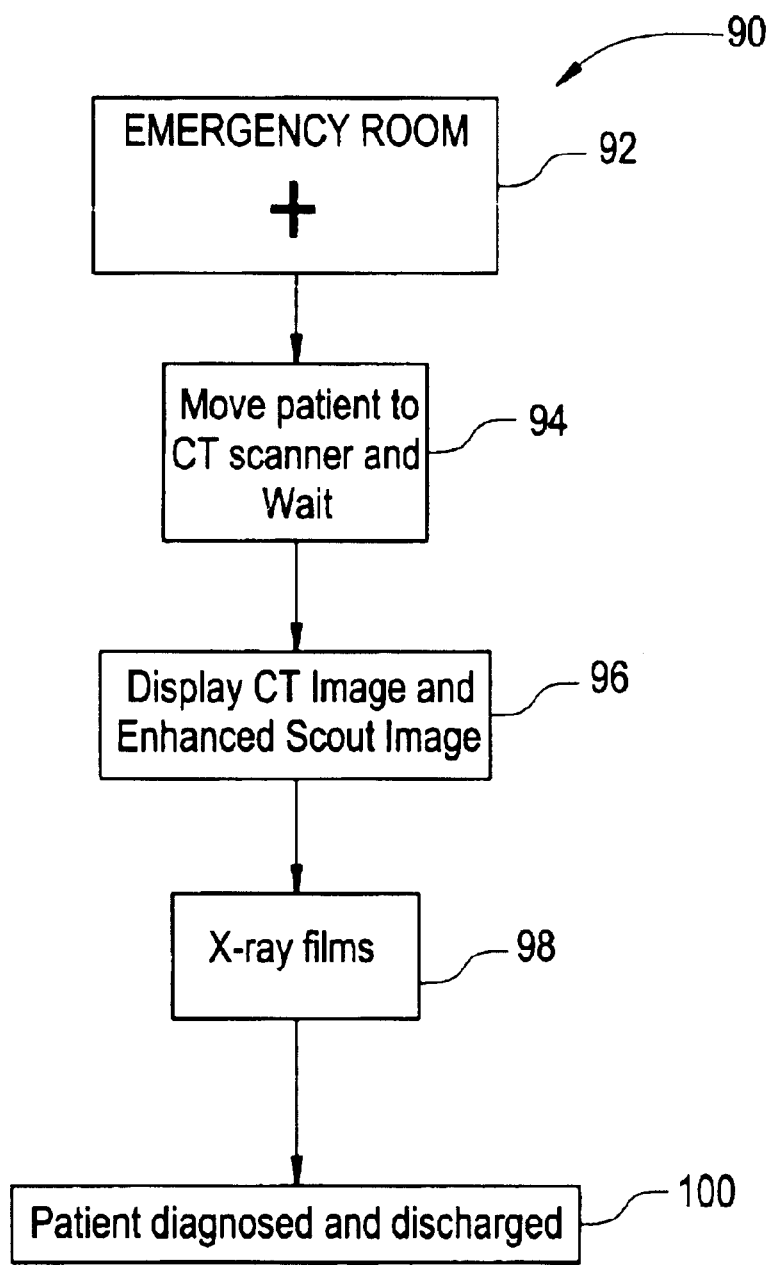

METHOD AND SYSTEM FOR TRAUMA APPLICATION OF CT IMAGING

BACKGROUND OF THE INVENTION

This invention relates generally to a method and apparatus for CT imaging and other radiation imaging systems and, more particularly, to utilizing an enhanced scout image for diagnostic purposes.

In at least some "computed tomography" (CT) imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated beam radiation received at a detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged, so the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent to the scintillator. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units," which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed.

In at least one known imaging system, a single scout image is generated by fixing the position of the x-ray source and translating the object in a z-axis direction. A resulting scout image, often called a scanogram, is similar to a plain radiography image. Using the scout image, an operator may identify anatomical landmarks.

However, the scout image generated from a single projection angle does not provide depth information regarding the object anatomy.

A plurality of scout scans are performed to generate depth information scout images of an object. Specifically, in order to generate at least one depth information scout image, the imaging system performs each scout scan at a different projection angle, or scout angle, with respect to the scanned object, e.g., patient. For example, as the patient is translated along a z-axis at a constant speed, a plurality of scout, or projection, data is collected as the position of a gantry is adjusted along a plurality of projection angles, or scout angles. However, apart from acting as a localizer, scout or projection data is not currently used for any diagnostic purposes. It should be noted that the scout is acquired using a relatively low current or very low mA. The enhanced scout in comparison is acquired at a higher mA, which is still comparable or even less than that with regular x-ray films.

Typically trauma scenarios in an emergency room (ER) setting require acquisition of preliminary C spine and L spine radiographs of trauma victims in a general rad room that is invariably followed by a CT scan in a separate CT scanner room, for example. More specifically, the protocol requires a combined set of planar x-ray films and CT scans, most likely taken in two different locations. The patient in most cases has suffered severe injury and is often greatly inconvenienced to be moved around. In addition, there is great loss of productivity in time taken in waiting for x-ray film development and waiting for the individual x-ray and CT scan stations. Complications could also develop as a result of the increased lengths of time trauma victims wait to be seen and scanned at each station.

It is therefore seen to be desirable to reduce the time expended in medical imaging in ER trauma applications. It is also desirable to reduce the waiting time between different medical imaging modalities.

BRIEF DESCRIPTION OF THE INVENTION

In one aspect, an imaging system is configured to generate a plurality of clinically useful images in a short time frame. A computed tomography system includes a computer, a gantry having a detector array, an x-ray source for radiating an x-ray beam along an imaging plane toward a detector array including a plurality of detector cells. The computer is coupled to the x-ray source and the gantry. The system is configured to generate a scout image configured to prescribe a tomographic axial/helical image or target image, process the scout image to generate an enhanced scout image, and display the enhanced scout image and target image, wherein the enhanced scout image and the target image are clinically useful images for diagnostic purposes provided by the single imaging system.

In another aspect, a processor in the imaging system is programmed to acquire projection data in a computed tomography system of an object. The processor generates a scout image configured to prescribe a target image, processes the scout projection data to generate an enhanced scout image, and displays the enhanced scout image and target image, wherein the enhanced scout image and target image are clinically useful Images for diagnostic purposes provided by the single imaging system.

In yet another aspect, a computer-readable medium in the imaging system is provided which comprises a stored program configured to generate a scout image configured to prescribe a target image, process the scout projection data to generate an enhanced scout image, and display the enhanced scout image and the target image, wherein the enhanced scout image and the target image are clinically useful images for diagnostic purposes provided by the single imaging system.

The above discussed and other features and advantages of the present invention will be appreciated and understood by those skilled in the art from the following detailed description and drawings.

BRIEF DESCRIPTION OF THE DRAWINGS

Referring to the exemplary drawings wherein like elements are numbered alike in the several Figures:

FIG. 5 is a flow chart illustrating an exemplary embodiment of a method for obtaining a scanned projection radiograph and a CT scan image from the CT scanner depicted in FIG. 1.

DETAILED DESCRIPTION OF THE INVENTION

Figure 1:
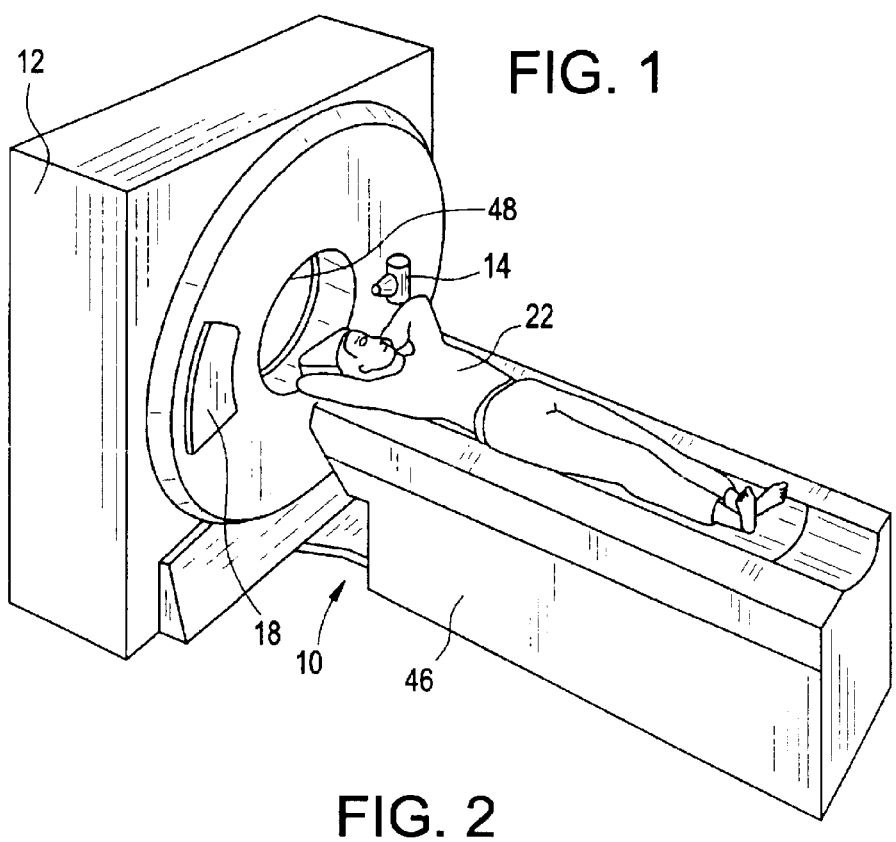
FIG. 1 is a pictorial view of a CT imaging system.
Figure 2:
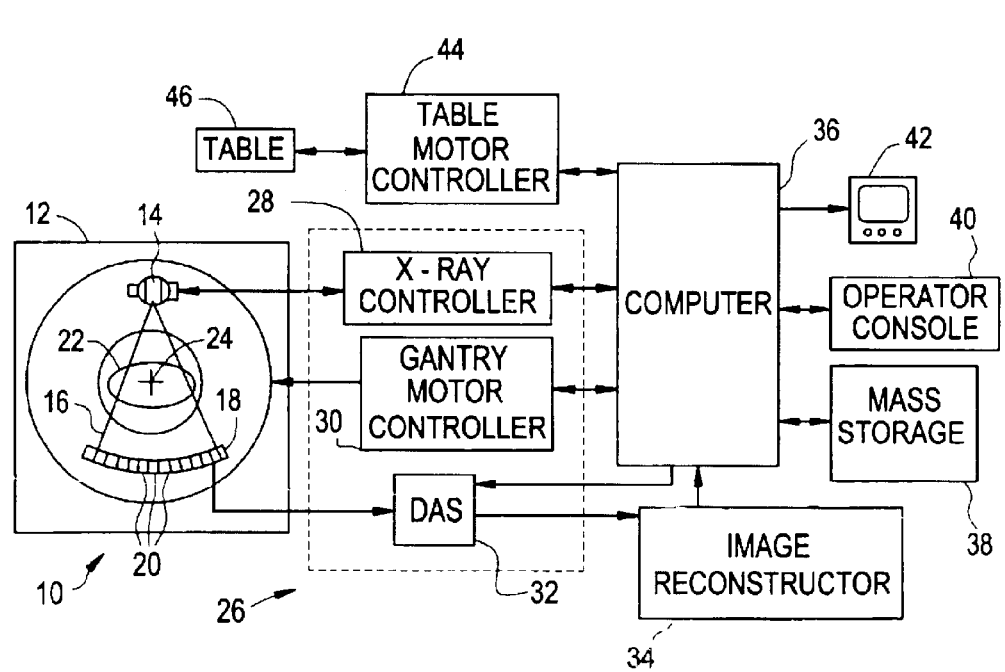
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
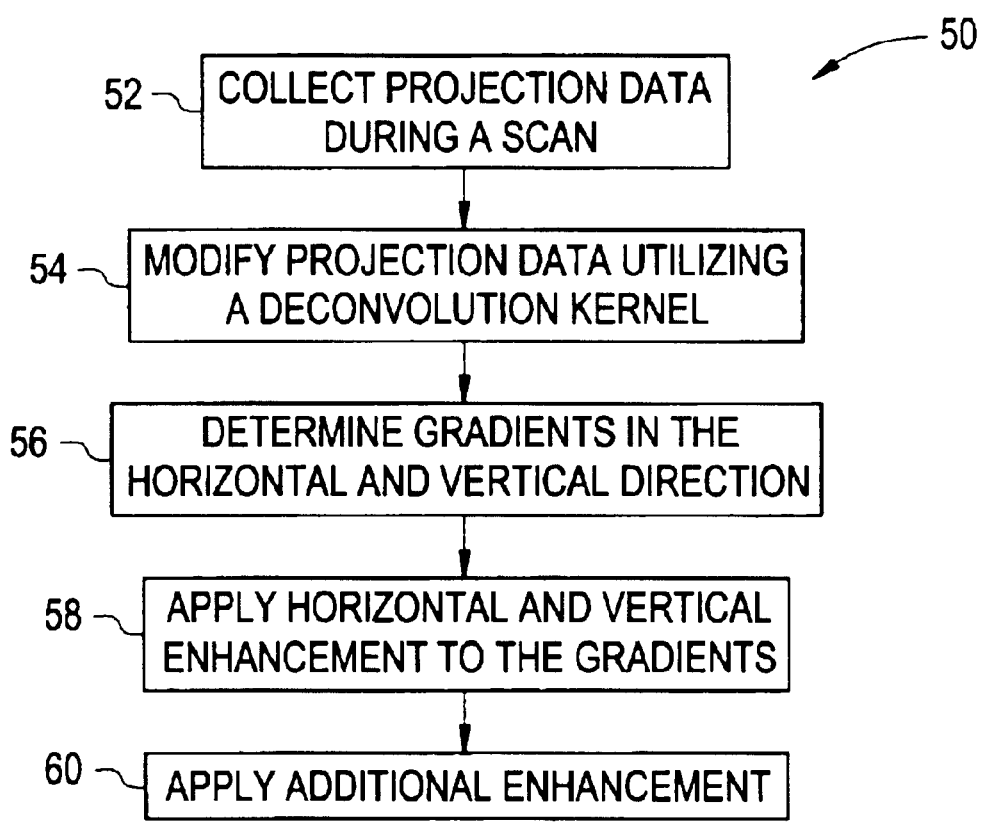
FIG. 3 is a flow chart illustrating the steps executed by the CT system for scout image processing.

FIG. 3 is a flow chart 50 illustrating the steps to improve spatial resolution during scout image processing. The method illustrated in FIG. 3 can be practiced by DAS 32 (shown in FIG. 2), image reconstructor 34 (shown in FIG. 2), or computer 36 (shown in FIG. 2). Generally, a processor in at least one of DAS 32, reconstructor 34, and computer 36 is programmed to execute the process steps described below. Of course, the method is not limited to practice in CT system 10 and can be utilized in connection with many other types and variations of imaging systems.

Referring specifically to FIG. 3, a set of raw scan data is acquired 52 during a scan, and the raw data is pre-processed to produce a projection. The data is resolved 54 in the z-direction to approximately the same resolution as the horizontal direction to be equivalent in resolution to a planar image. Then, a horizontal gradient and a vertical gradient are determined 56 by determining a variation between samples in the horizontal and vertical direction. Weights are calculated based on the horizontal and vertical variance. Different weights are then applied to the horizontal and vertical gradients and a desired amount of enhancement is applied 58 to the weighted gradients. Then, additional enhancement is applied 60.

During scout scanning, gantry 12 is not rotated but remains stationary while table 46 moves through gantry opening 48. Referring specifically to FIG. 3, projection data is acquired 52 for a view from a particular gantry angle relative to patient 22 as patient table 46 travels at 100 mm/s in the z-axis direction while DAS 32 samples at 500 Hz. in one embodiment, approximately twelve projection views are collected per detector cell thickness. Then, six adjacent views are summed to obtain an inter-pixel distance that is approximately equal to a sampling distance in an x-direction, e.g., horizontal direction. The distance between adjacent samples near the iso-center is approximately 0.58 mm because of the magnification of the fan beam sampling geometry. The simple summation process will degrade the z-axis resolution, e.g., vertical resolution, which is already significantly worse than the x-axis direction resolution, e.g., horizontal resolution, without the summation.

To improve spatial resolution, a deconvolution process is utilized. A modified sample, p'(i,j), Is obtained by convolving an original sample, p(ij), with a deconvolution kernel, θ(j), to reduce an effective thickness below a detector aperture size. U.S. Pat. No. 6,366,638 assigned to the same assignee of this application outlines an exemplary deconvolution process that may be employed to generate an enhanced scout image and is incorporated by reference herein in its entirety.

Many techniques can be utilized to derive the deconvolution kernel, θ(j) and are well know in the pertinent art. For example, in one embodiment, a "singular value decomposition" (SVD) technique is utilized to derive the kernel based on a system point spread function. In an alternative embodiment, the first n views, e.g., n<6, is summed from a set of intermediate samples to reduce image noise. These intermediate samples are then processed with a deconvolution kernel to generate a set of samples with improved spatial resolution. For example, in an exemplary embodiment, three views are summed. Within the three views, the maximum deviation from the center sample is only 0.1 mm; therefore, the impact on spatial resolution is kept to a minimum. A five-point deconvolution kernel is then applied to these samples to arrive at the enhanced samples. In an alternative embodiment, the deconvolution processing can be carried out in frequency space. A Fourier transform of an original scout is obtained multiplied by a deconvolution filter. The result is then processed though an inverse Fourier transform to produce an enhanced scout.

In one embodiment, increased enhancement is utilized to increase image resolution of small pathologies, such as kidney stones having low density. By utilizing enhanced scout images overshoot and undershoot are essentially eliminated, and the image does not appear to be artificial, but has a "look" of a typical x-ray film. Thus, a separate x-ray in a general rad room can be eliminated and the CT scanner can be solely utilized to generate CT enhanced scout images replicating a typical x-ray, as well as CT tomographic axial/helical or target images.

Figure 4:
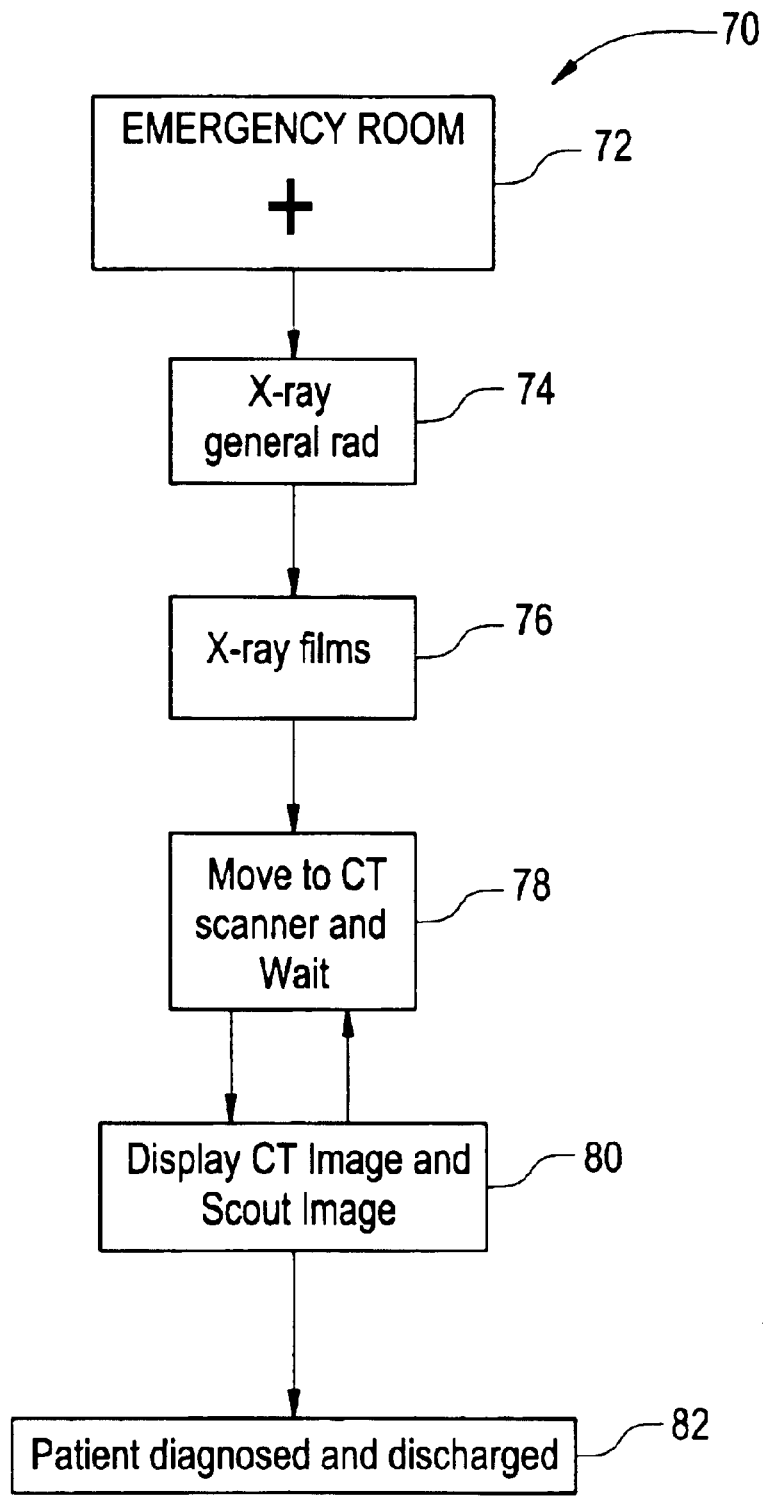
FIG. 4 is a flow chart illustrating the steps executed in a conventional trauma scenario necessitating x-ray film radiographs obtained in a general rad room and a CT scan in a separate CT scanner room.

Referring now to FIG. 4, steps presently taken in a trauma situation are exemplified generally at 70. More specifically, upon admission to an emergency room (ER), the patient waits therein to be diagnosed or screened with a medical imaging device at block 72. For example, in most trauma scenarios in the ER setting, preliminary C spine and L spine radiographs are acquired in a general rad room at block 74 to generate x-ray films at block 76. X-rays in the general rad room are invariably followed by a CT scan in a CT scanner room indicated at block 78, which means the patient is moved from one medical image modality to another. A scout image is displayed for obtaining anatomical landmarks for acquiring a desired target image from the CT scanner at block 80. The patient in most cases has suffered severe injury and is often greatly inconvenienced to be moved around. In addition, there is a great loss of productivity by waiting for x-ray film development and waiting for availability of the x-ray and CT scans. Furthermore, complications could potentially develop as a result of the increased lengths of time trauma victims wait to be imaged by the above modalities. In many cases after the patient is imaged with the two imaging modalities, the medical diagnosis indicates no immediate medical damage and the patient is discharged from the medical facility altogether. In this case, the patient is diagnosed and discharged after considerable time has been expended between two different imaging modalities in the ER. Alternatively, after the patient is diagnosed, the patient is discharged from the ER and directed to seek further medical treatment indicated at block 82.

FIG. 5 illustrates a method generally at 90 by which a single CT scanner generates a target image and an enhanced scout image, wherein the enhanced scout image eliminates the need for the patient to be separately x-rayed in a general rad room or with a different medical imaging modality other than with the CT scanner 10. More specifically, after the patient is admitted and waits in the ER at block 92, the patient may be next transported to CT scanner 10 at block 94. An enhanced CT scout is taken on the CT scanner table 46 as part of the CT scan. Hence, there is no additional apparatus required to perform a scan that replicates an x-ray scan taken in a separate general rad room. Trauma patients can greatly benefit by being admitted directly to the CT scanner room which could then provide the radiologist with the scanned projection radiograph images instantaneously at block 96 along with the target image from CT scanner 10. If needed, the scanned projection radiographs may be generated in hard copy form at block 98 to replicate the conventional x-ray film used for diagnostic purposes by medical practitioners. After the patient is imaged and diagnosed as a result of the images, the patient is discharged from the ER indicated at block 100. The enhanced CT scout serves as a one stop solution.

The CT enhanced images are produced immediately after the scan is taken. It serves as a localizer in addition to serving as an x-ray radiograph. Physicians can decide course of action immediately when the patient is still lying on the table. This can facilitate a reduction in the wastage of time especially for a trauma victim and can quicken the time for treatment and diagnosis. The x-ray like CT enhanced scout can be printed on films as soon as the images are produced. The images can easily be transferred and archived. For example, the images may be transferred via propagation of a signal to another computer for storage therein and/or for outputting a hard copy film thereof. Most importantly, the patient is not moved and a complete diagnosis can be made with increased productivity. The invention thus not only promotes hospital productivity while providing a shorter inpatient stay and improved care. Furthermore, scout scans are automatically created to be as long as you want it since they are created online and provide images immediately. For example, scout scans are used In urography where the scout scans follow the contrast agent as it flows through the renal system. This is a significant advantage over x-ray systems.

In accordance with an exemplary embodiment, processing of FIGS. 3 and 5 may be implemented through processing device 40 operating in response to a computer program. In order to perform the prescribed functions and desired processing, as well as the computations therefore, the controller may include, but not be limited to, a processor(s), computer(s), memory, storage, register(s), timing, interrupt (s), communication interfaces, and input/output signal interfaces, as well as combinations comprising at least one of the foregoing. For example, the controller may include signal input signal filtering to enable accurate sampling and conversion or acquisitions of such signals from communications interfaces. It is also considered within the scope of the invention that the processing depicted in FIGS. 3 and 5 may be implemented by a controller located remotely from processing device 40. It will be recognized that if a user prefers to obtain both non-diagnostic scout and diagnostic enhanced scout images, the enhanced image scout may also be used for localization purposes.

As described above, the present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) can be updated to implement the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments failing within the scope of the appended claims. Moreover, the use of the terms first, second, etc. do not denote any order or importance, but rather the terms first, second, etc. are used to distinguish one element from another.

What is claimed is:

1. A method for generating a plurality of clinically useful images in a short time frame using a single imaging system, the method comprising:
   generating a scout image configured to prescribe a target image;
   processing said scout image to generate an enhanced scout image; and
   displaying said enhanced scout image and said target image, wherein said enhanced scout image and said target image are clinically useful images for diagnostic purposes provided by the single imaging system.

2. The method of claim 1, wherein said enhanced scout image is a scanned projection radiograph.

3. The method of claim 1, wherein said enhanced scout image is generated as in a planar x-ray developed film.

4. The method of claim 1, wherein said enhanced scout image is at least one of transferred and archived via propagation of an electrical signal representative thereof.

5. The method of claim 4, wherein after said propagation of an electrical signal representative thereof, said enhanced projection radiograph is generated as in a planar x-ray developed film.

6. The method of claim 1, wherein said generating said scout image acts as a localizer in obtaining said target image in addition to serving in generating an x-ray radiograph.

7. The method of claim 1, wherein said target image is a CT scan image.

8. The method of claim 1, further comprising:
   obtaining projection data for at least one scout scan; and
   modifying said projection data utilizing a deconvolution kernel to generate said enhanced scout image.

9. The method of claim 1, wherein said enhanced scout image and said target image are displayed on one of a single display device and a two separate display devices.

10. A single imaging system configured to generate a plurality of clinically useful images in a short time frame comprising:
    a computed tomography system comprising a computer, a gantry having a detector array, an x-ray source for radiating an x-ray beam along an imaging plane toward a detector array including a plurality of detector cells, the computer coupled to the x-ray source and the gantry, said system configured to:
    generate a scout image configured to prescribe a target image;
    process said scout image to generate an enhanced scout image; and
    display said enhanced scout image and said target image, wherein said enhanced scout image and said target image are clinically useful images for diagnostic purposes provided by the single imaging system.

11. The system of claim 10, wherein said enhanced scout image is a scanned projection radiograph.

12. The system of claim 10, wherein said enhanced scout image is generated as in a planar x-ray developed film.

13. The method of claim 10, wherein said enhanced scout image is at least one of transferred and archived via propagation of an electrical signal representative thereof.

14. The method of claim 13, wherein after said propagation of an electrical signal representative thereof, said enhanced projection radiograph is generated as in a planar x-ray developed film.

15. The method of claim 10, wherein said generating said scout image acts as a localizer in obtaining said target image in addition to serving in generating an x-ray radiograph.

16. The method of claim 10, wherein said target image is a CT scan image.

17. The method of claim 10, further comprising:
    obtaining projection data for at least one scout scan; and
    modifying said projection data utilizing a deconvolution kernel to generate said enhanced scout image.

18. The method of claim 10, wherein said enhanced scout image and said target image are displayed on one of a single display device and a two separate display devices.

19. A method for generating two diagnostic images of an object using a single computed tomography (CT) imaging system, the CT system including an x-ray tube for emitting x-ray beams and a detector aligned with the x-ray tube for receiving the x-ray beams, said method comprising:
    generating a scout image configured to prescribe a target image;
    processing said scout image to generate an enhanced scout image; and
    displaying said enhanced scout image and said target image, wherein said enhanced scout image and said target image are clinically useful images for diagnostic purposes provided by the single imaging system.

20. The method of claim 19, wherein said enhanced scout image is generated as in a planar x-ray developed film.

21. The method of claim 19, wherein said enhanced scout image is at least one of transferred and archived via propagation of an electrical signal representative thereof.

22. The method of claim 21, wherein after said propagation of an electrical signal representative thereof, said enhanced projection radiograph is generated as in a planar x-ray developed film.

23. The method of claim 19, wherein said generating said scout image acts as a localizer in obtaining said target image in addition to serving in generating an x-ray radiograph.

24. A computed tomography (CT) system for generating two diagnostic images of an object, said CT system comprising an x-ray tube for emitting x-ray beams and a detector aligned with said x-ray tube for receiving said x-ray beams, said system configured to:
    generate a scout image configured to prescribe a target image;
    process said scout image to generate an enhanced scout image; and
    display said enhanced scout image and said target image, wherein said enhanced scout image and said target image are clinically useful images for diagnostic purposes provided by the single imaging system.

25. The system of claim 24, wherein said enhanced scout image is generated as in a planar x-ray developed film.

26. The system of claim 24, wherein said enhanced scout image is at least one of transferred and archived via propagation of an electrical signal representative thereof.

27. The method of claim 26, wherein after said propagation of an electrical signal representative thereof, said enhanced projection radiograph is generated as in a planar x-ray developed film.

28. The method of claim 24, wherein said generating said scout image acts as localizer in obtaining said target image in addition to serving in generating an x-ray radiograph.

29. A processor programmed to reconstruct scout images in a computed tomography system, said processor configured to:
- generate a scout image configured to prescribe a target image;
- process said scout image to generate an enhanced scout image; and
- display said enhanced scout image and said target image, wherein said enhanced scout image and said target image are clinically useful images for diagnostic purposes provided by the single imaging system.

30. A computer-readable medium in an imaging system, said computer-readable medium comprising a stored program configured to:
- generate a scout image configured to prescribe a target image;
- process said scout image to generate an enhanced scout image; and
- display said enhanced scout image and said target image, wherein said enhanced scout image and said target image are clinically useful images for diagnostic purposes provided by the single imaging system.

* * * * *